(12) United States Patent
McNeal et al.

(10) Patent No.: US 7,215,428 B2
(45) Date of Patent: May 8, 2007

(54) ABSORPTION SPECTROSCOPY APPARATUS AND METHOD

(75) Inventors: Mark P. McNeal, Marlborough, MA (US); Peter G. Loges, Natick, MA (US); Irina Puscasu, Brighton, MA (US); James T. Daly, Mansfield, MA (US); Edward A. Johnson, Bedford, MA (US)

(73) Assignee: Ion Optics, Inc., Waltham, MA (US)

( * ) Notice: Subject to any disclaimer, the term of this patent is extended or adjusted under 35 U.S.C. 154(b) by 122 days.

(21) Appl. No.: 11/101,913

(22) Filed: Apr. 8, 2005

(65) Prior Publication Data

US 2006/0227327 A1 Oct. 12, 2006

(51) Int. Cl.
*G01N 21/61* (2006.01)
(52) U.S. Cl. ....................... 356/440; 356/246
(58) Field of Classification Search ................ 356/440, 356/246; 250/343
See application file for complete search history.

(56) References Cited

U.S. PATENT DOCUMENTS

| | | | |
|---|---|---|---|
| 3,994,603 A * | 11/1976 | Paschedag | ............... 356/438 |
| 4,322,621 A | 3/1982 | Aagard | |
| 4,749,276 A | 6/1988 | Bragg et al. | |
| 5,024,526 A * | 6/1991 | von Redwitz | ............... 356/73 |
| 5,220,402 A | 6/1993 | Harvey | |
| 5,440,143 A | 8/1995 | Carangelo et al. | |
| 5,459,566 A | 10/1995 | Pearson et al. | |
| 5,485,276 A | 1/1996 | Bien et al. | |
| 5,488,227 A * | 1/1996 | Sweet | ............... 250/343 |
| 5,714,759 A | 2/1998 | Nelson | |
| 5,726,752 A | 3/1998 | Uno et al. | |
| 5,731,583 A | 3/1998 | Bailey et al. | |
| 5,818,578 A | 10/1998 | Inman et al. | |
| 5,949,537 A | 9/1999 | Inman et al. | |
| 2002/0185603 A1 | 12/2002 | Daly et al. | |

* cited by examiner

*Primary Examiner*—Richard A. Rosenberger
(74) *Attorney, Agent, or Firm*—Mark G. Lappin; Foley & Lardner LLP (57) ABSTRACT

An absorption spectroscopy apparatus including a sample cell having a central axis, and a side wall coaxially positioned about the axis. The side wall defines a generally circular cross-section of the cell as taken along a plane extending perpendicular to the axis, wherein the generally circular cross-section of the sample cell has an average radius. The side wall includes a plurality of light reflective segments arrayed about the axis, wherein each reflective segment has a cross-section taken along a plane extending perpendicular to the axis of the cell that is concave with respect to the axis. The concave cross-section of each segment has an average radius that is unequal to the average radius of the generally circular cross-section of the sample cell. Among other aspects and advantages, the apparatus of the present disclosure is able to use incoherent, non-collimated light sources while maintaining high optical throughput efficiencies.

21 Claims, 11 Drawing Sheets

ABSORPTION SPECTROSCOPY APPARATUS AND METHOD

FIELD OF THE DISCLOSURE

The present disclosure relates generally to spectrophotometric techniques for analyzing the content of a given fluid and, more particularly, to an apparatus for optimizing the sensitivity of such analysis. Even more particularly, the present disclosure relates to a new and improved multi-pass sample cell for use in absorption spectroscopy and an absorption spectroscopy apparatus incorporating the cell.

BACKGROUND OF THE DISCLOSURE

Spectroscopy systems and methods are used to analyze the composition of various types of materials, including gases, liquids and the like. Spectroscopy is based on the fact that different chemical compositions absorb energy, e.g., light, at different frequencies, so that measuring the intensity versus the frequency of the light passed through a sample can be used to identify which light frequencies were absorbed by the sample and which were not. Thus, the chemicals present in the sample can be readily identified. Spectroscopy systems and methods also can identify the amount of light absorbed by the sample at each given frequency. Thus, the quantity of each chemical present in the chemical composition can be determined. In addition, such analysis can be performed with any one of various different ranges of light such as infrared, ultraviolet and the like, each of which pertains to a separate range of frequencies.

An absorption cell (or resonator), which holds the gas or liquid sample through which light is passed, is used to perform spectroscopy analysis in conjunction with suitable spectroscopy equipment, such as a collimated laser light and a light detector. It has long been realized that to increase the sensitivity in providing both quantitative and qualitative analyses, the collimated laser light must be passed through a very large percentage of the available sample. Thus, absorption cells have been provided with "folded" light paths, in which mirrors reflect the light back and forth within the cell, such that the light makes multiple passes through the sample. The folded light path increases the optical path length between the laser and the light detector to thereby increase the sensitivity of a spectroscopy system incorporating an absorption cell producing a folded light path. Examples of existing "multi-pass" absorption cells are shown in U.S. Pat. Nos. 4,322,621; 4,749,276; 5,220,402; 5,440,143; 5,459,566; 5,485,276; 5,714,759; 5,731,583; 5,726,752; 5,818,578; and 5,949,537.

U.S. Patent Application Publication No. 2002/0185603 A1 ('603 publication), which is owned by the assignee of the present application, discloses an improved "multi-pass" absorption cell that increases the optical path length without greatly increasing the size or volume of the sample cell and causes light to pass through a very large percentage of a sample contained in the cell. The improved absorption cell of the '603 publication prevents the loss of significant amounts of light through ends of the cell and provides a large throughput, or etendue, so that the amount of light that can be directed through the sample and the sensitivity of the resulting measurement can be increased. In addition, the improved absorption cell of the '603 publication is robust and relatively easy to manufacture.

What is still desired is a new and improved multi-pass sample cell for use in absorption spectroscopy. Among other advantages and aspects, the new and improved multi-pass sample cell preferably will allow an absorption spectroscopy apparatus incorporating the cell to use light sources that are not collimated. In addition, the new and improved multi-pass sample cell preferably will minimize the difference (dispersion) in path lengths experienced by angularly divergent light rays traversing the sampling cell. The new and improved multi-pass sample cell preferably will also maintain or improve path length and throughput efficiency. Moreover, the new and improved multi-pass sample cell preferably will allow very high gas flow through the sampling cell while causing minimum disruption and turbulence to the gas flow. Furthermore, an absorption spectroscopy apparatus incorporating the new and improved multi-pass sample cell preferably will have a smaller total package size, including the source, the detector, the launch optics and the sample cell, in order to be fitted on existing flow streams.

SUMMARY OF THE DISCLOSURE

The present disclosure provides a new and improved multi-pass sample cell and an absorption spectroscopy apparatus incorporating the cell. An exemplary embodiment of the sample cell includes a central axis and a side wall coaxially positioned about the central axis. The side wall defines a generally circular cross-section of the sample cell as taken along a plane extending perpendicular to the axis of the cell, and the generally circular cross-section of the sample cell has an average radius. The side wall includes a plurality of light reflective segments arrayed about the axis, and each reflective segment has a cross-section taken along a plane extending perpendicular to the axis of the cell that is concave with respect to the axis. The concave cross-section of each segment has a radius that is different than the average radius of the generally circular cross-section of the sample cell.

Among other benefits, the improved absorption spectroscopy apparatus of the present disclosure enables light to be passed through a very large percentage of a sample passing through the sample cell. The cell is constructed so as to be small and compact while nonetheless enabling the light to make successive passes through the sample. The concave segments of the side wall have been found to minimize differences (dispersion) in path lengths experienced by angularly divergent rays traversing through the sampling cell, while increasing path lengths and increasing throughput efficiency. Moreover, the sample cell of the present disclosure greatly relaxes beam collimation requirements; that is, it advantageously facilitates the use of widely available, inexpensive thermal sources as opposed to requiring expensive infrared lasers. The sample cell of the present disclosure improves path length, efficiency, spatial uniformity, and high fluid throughput (open path design) using cheaper, readily available less-collimated light sources.

According to one embodiment of the sample cell of the present disclosure, the radii of the concave cross-sections of the segments of the side wall are each greater than the average radius of the generally circular cross-section of the sample cell. According to another embodiment, the radii of the concave cross-sections of the segments of the side wall are each at least two times greater than the average radius of the generally circular cross-section of the sample cell.

In an additional embodiment of the sample cell of the present disclosure, the radii of the concave cross-sections of the reflective segments of the side wall pass through the axis of the sample cell. According to another embodiment, the light reflective segments of the side wall are equally arrayed about the axis.

In a further embodiment of the sample cell of the present disclosure, each of the reflective segments of the side wall of the cell has a cross-section taken along a plane extending parallel to the axis of the cell that is planar. However, according to yet another embodiment, each of the reflective segments of the side wall of the cell has a cross-section taken along a plane extending parallel to the axis of the cell that is concave with respect to the axis.

These and other advantages and aspects of the present disclosure will become apparent to those skilled in the art after a reading of the following description of exemplary embodiments when considered with the drawings.

BRIEF DESCRIPTION OF DRAWINGS

The present disclosure is described with reference to the accompanying drawings, wherein.

Like reference characters designate identical or corresponding components and units throughout the several views. In addition, x, y, and z coordinates are illustrated in some of the drawings for reference only.

DETAILED DESCRIPTION OF EXEMPLARY EMBODIMENTS

Figure 1:
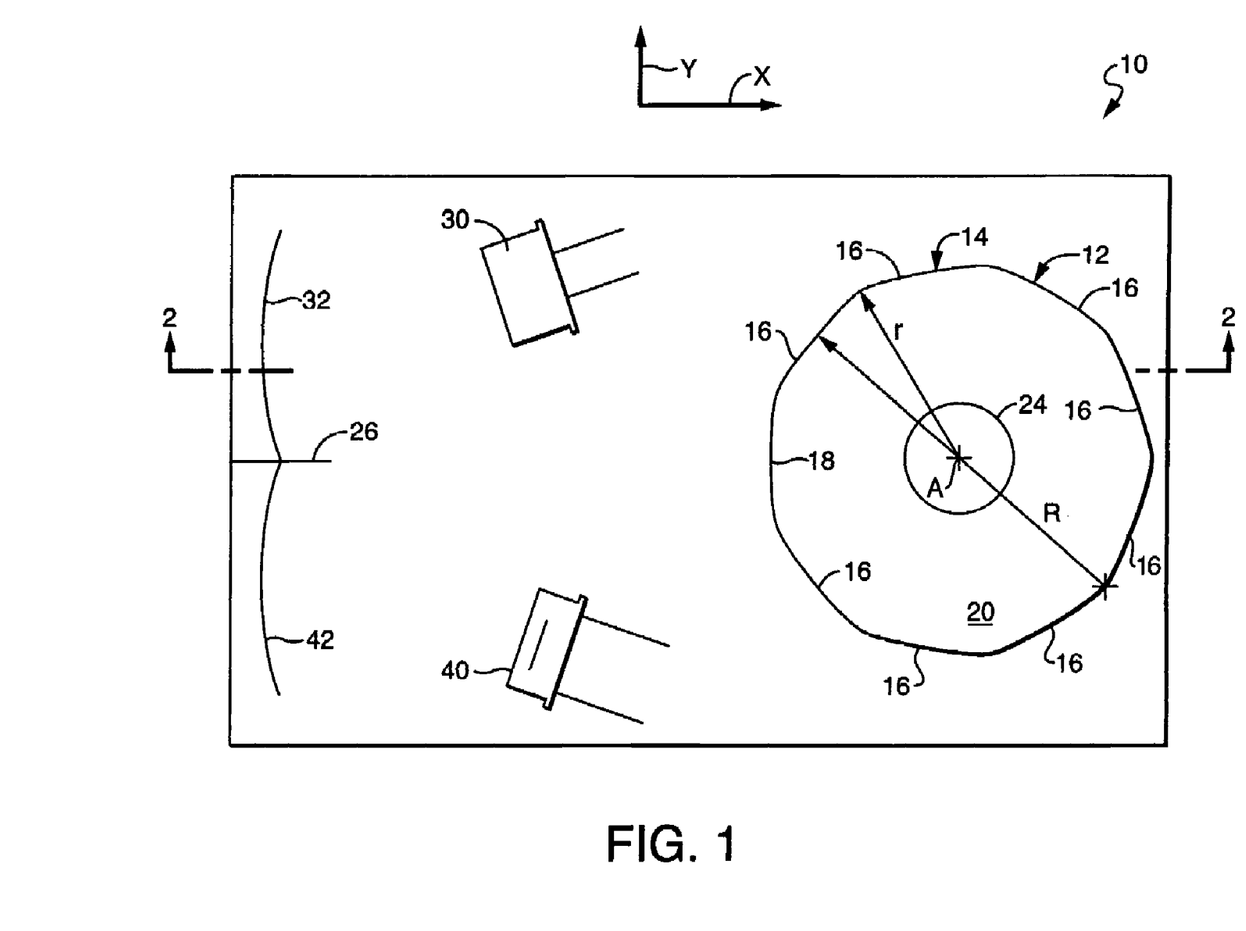
FIG. 1 is a schematic top view of an exemplary embodiment of an improved absorption spectroscopy apparatus constructed in accordance with the present disclosure, wherein an end wall of the apparatus is removed to show a light source, a light detector, launch and collection reflectors and a multi-pass sample cell.
Figure 2:
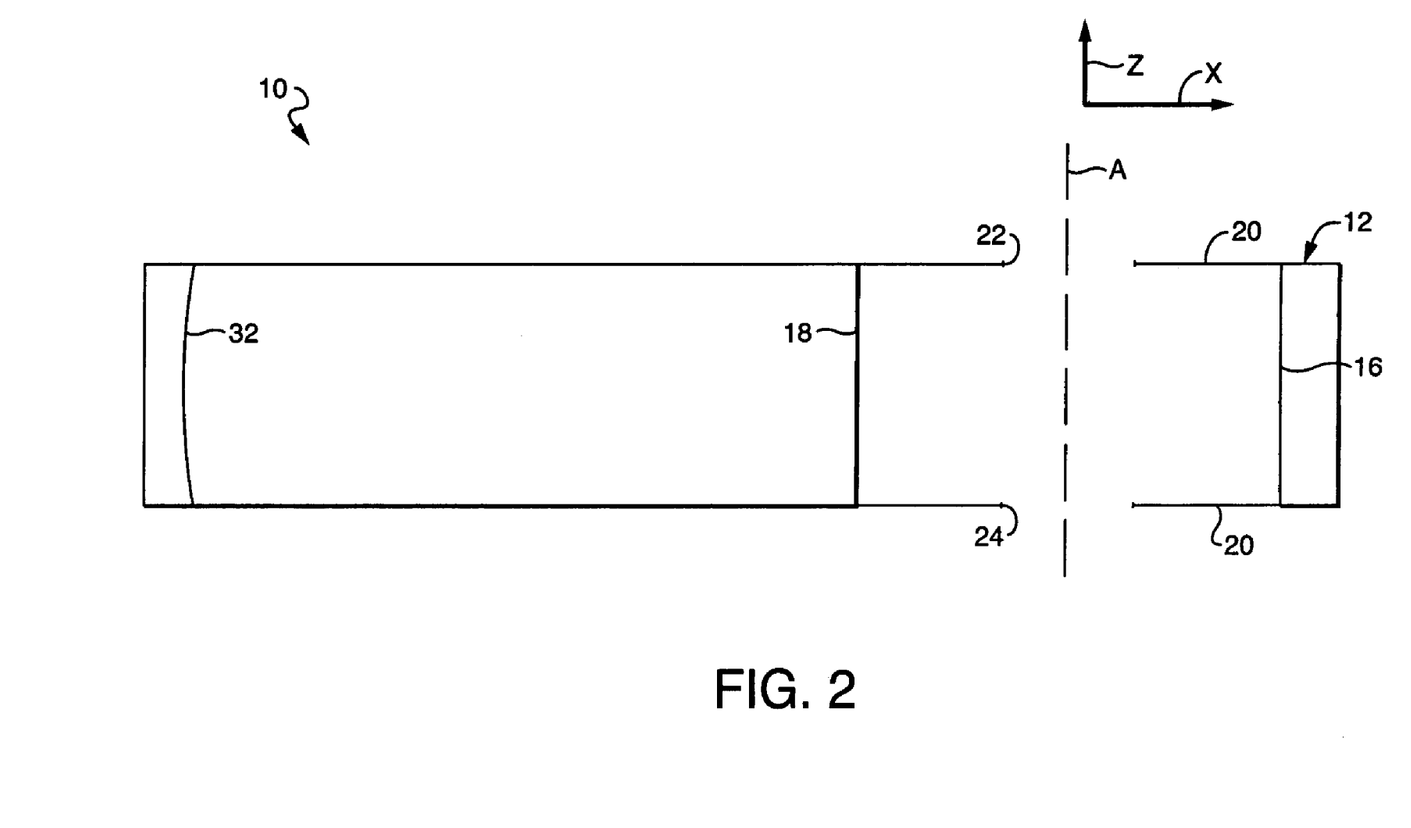
FIG. 2 is a schematic side view of the absorption spectroscopy apparatus of FIG. 1, illustrating a sectional view of the launch reflector and the sample cell as taken along line 2—2 of FIG. 1.

Referring to FIGS. 1 and 2 of the drawings, there is shown a schematic representation of an exemplary embodiment of a new and improved absorption spectroscopy apparatus 10 constructed in accordance with the present disclosure. The apparatus 10 includes a light source 30, a light detector 40, and launch and collection reflectors 32, 42. The apparatus 10 also includes a multi-pass, fluid sample cell 12 having a side wall 14 coaxially arranged about a central axis A of the cell 12. As shown best in FIG. 1, the side wall 14 defines a generally circular cross-section of the sample cell 12 as taken along a plane extending perpendicular to the axis A of the cell (i.e., the x-y plane as illustrated in the drawings), and the generally circular cross-section of the sample cell 12 has an average radius r. The side wall 14 includes a plurality of light reflective segments 16 arrayed about the axis A, and each reflective segment 16 has a cross-section taken along a plane extending perpendicular to the axis (i.e., the x-y plane as illustrated in the drawings) that is concave with respect to the axis A. The concave cross-section of each segment 16 has an average radius R that is unequal to the average radius r of the generally circular cross-section of the sample cell 12.

Among other aspects and benefits, the new and improved absorption spectroscopy apparatus 10 of the present disclosure enables light to be passed through a very large percentage of a sample passing through the sample cell 12. The cell 12 is constructed so as to be small and compact while nonetheless enabling the light to make successive passes through the sample. The concave segments 16 of the side wall 14 have been found to minimize differences (dispersion) in path lengths experienced by angularly divergent rays traversing through the sampling cell 12, while increasing path lengths and increasing throughput efficiency. Moreover, the sample cell 12 of the present disclosure greatly relaxes beam collimation requirements; that is, it advantageously facilitates the use of widely available, inexpensive thermal sources as opposed to requiring expensive infrared lasers.

Figure 3:
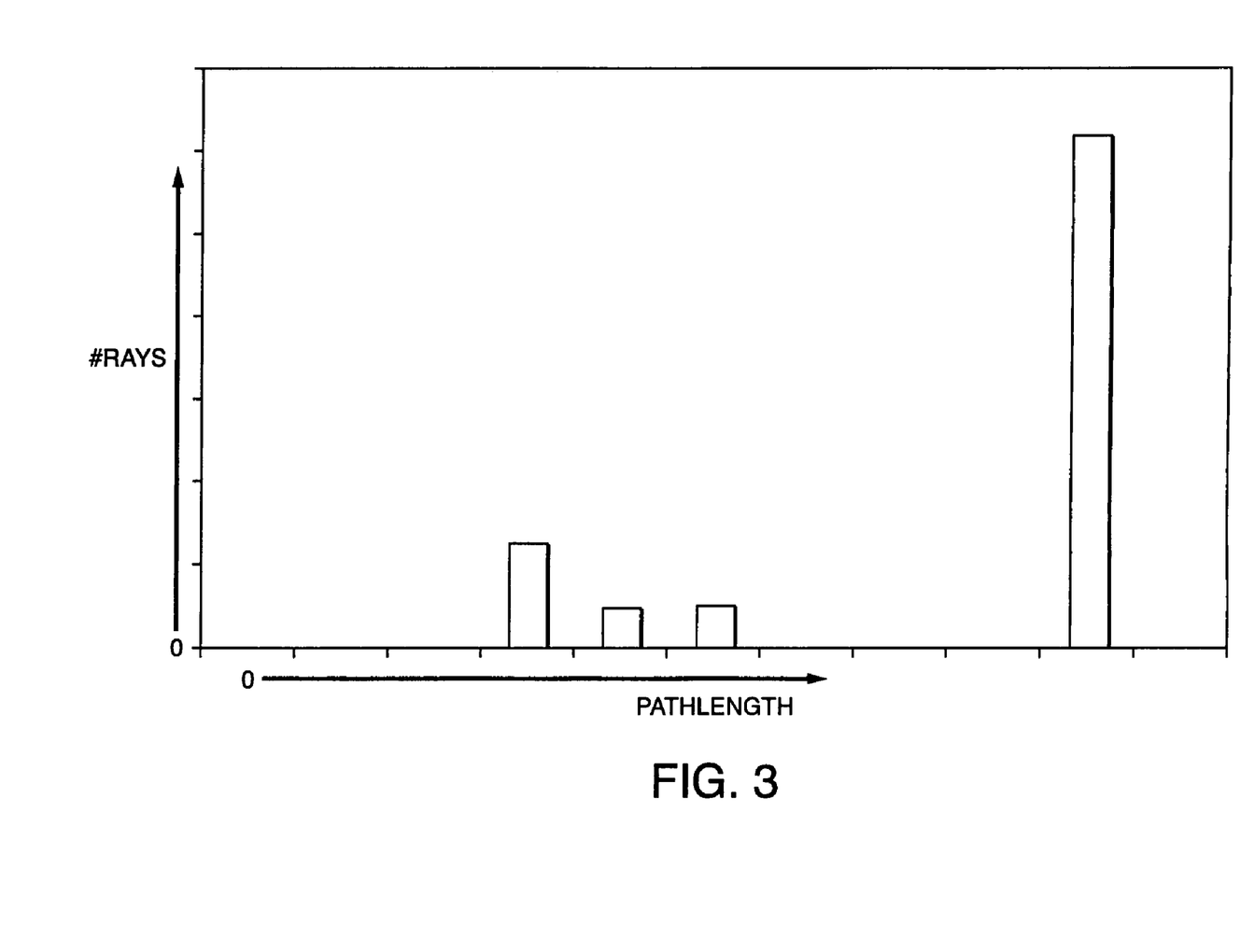
FIG. 3 is a histogram of path lengths experienced by rays traversing the multi-pass cell of the absorption spectroscopy apparatus of FIG. 1.

For example, in FIG. 3 there is shown a histogram of path lengths experienced by light rays traversing the multi-pass sample cell 12 of the absorption spectroscopy apparatus 10 of FIG. 1. As illustrated by the histogram, the sample cell 12 of the present disclosure minimize differences (dispersion) in path lengths experienced by different rays traversing through the sampling cell 12, while increasing the path lengths. In particular, the histogram shows that the multi-pass sample cell 12 of FIGS. 1 and 2 causes the vast majority of rays to have the same path length. In addition, the vast majority of rays are provided with a relatively long path length.

In the exemplary embodiment shown in FIG. 1, the average radii of the concave cross-sections of the segments 16 of the side wall 14 are each greater than the average radius of the generally circular cross-section of the sample cell 12. In particular, the average radii of the concave cross-sections of the segments 16 of the side wall 14 are each at least two times greater than the average radius of the generally circular cross-section of the sample cell 12.

As shown best in FIG. 1, in the exemplary embodiment illustrated, the light reflective segments 16 of the side wall 14 are equally arrayed about the axis A, and are oriented such that each of the radii R of the reflective segments 16 of the side wall 14 passes through the axis A of the sample cell 12. In addition, the average radii R of the concave cross-sections of the segments 16 of the side wall 14 are equal. In alternative embodiments, however, the segments 16 of the side wall 14 may be provided with radii that are not equal, if desired, such that some segments may be larger than others. In the exemplary embodiment of FIG. 1, the average radius R of each of the concave cross-sections of the segments 16 of the side wall 14 each comprise a constant radius R, such that the concave cross-sections comprise a portion of a circle. In alternative embodiments, however, one or all of the segments 16 of the side wall 14 could be provided with a radius that is not constant, such that the concave cross-sections would not comprise a portion of a circle (e.g., the concave cross-sections might comprise a portion of an ellipse, or may be comprised of smaller, planar sub-segments).

As shown best in FIG. 2, each of the reflective segments 16 of the side wall 14 of the cell 12 has a cross-section taken along a plan extending parallel to the axis A of the cell 12 (e.g., the x-z plane as illustrated in the drawings) that is planar.

Referring to both FIGS. 1 and 2, the side wall 14 of the cell 12 also includes at least one transparent segment 18 for allowing a ray of light from the source 30 to pass into the cell 12, and a ray of light to pass out of the cell 12 to the detector 40. In the exemplary embodiment shown, the transparent segment 18 has a flat profile. The cell 12 further includes opposing, flat end walls 20, which together with the side wall 14 form an enclosed cell 12. The end walls 20 include sample inlet and outlet ports 22, 24 that are used to bring fluid samples into the interior cavity and remove the samples from the cell 12. The end walls 20 may be provided with inwardly facing reflective surfaces.

The apparatus 10 is provided with separate launch and collection reflectors 32, 42 separated by a baffle 26, as shown best in FIG. 1, in order to eliminate optical cross-talk between the source 30 and the detector 40 packages. Each of the launch and collection reflectors 32, 42 is provided with a concave cross-section as viewed from an end of the reflectors, as shown best in FIG. 1. In addition, each of the launch and collection reflectors 32, 42 has a concave cross-section as viewed from a side of the reflectors, as shown best in FIG. 2. The launch and collection reflectors 32, 42, therefore, include a toroidal reflective surface facing the transparent segment 18 of the sample cell 12. The toroidal reflective surfaces 32, 42 act to focus light beams that are reflected off those surfaces.

The light source 30 and the launch reflector 32 are positioned and oriented such that a ray of light emitted by the light source 30 is reflected off the launch reflector 32 and through the transparent segment 18 of the sample cell 12. The light detector 40 and the collection reflector 42 are positioned and oriented such that a ray of light reflected through the transparent segment 18 of the sample cell 12 from one of the reflective segments 16 of the sample cell 12, are then reflected off the collection reflector 42 to the light detector 40.

Light directed through the transparent segment 18 of the sample cell 12 to a predetermine point on one of the reflective segments 16 of the side wall 14 commences a step-by-step progression of the back-and-forth reflections of such energy through the sample cell 12. Within the generally circular configuration of the side wall 14 of the cell 12, the light is reflected back-and-forth on or from the curved reflective segments 16 until the energy is directed back through the transparent segment 18 of the sample cell 12, off the collection reflector 42, and to the light detector 40 for reading the energy absorption that has taken place by the sample within the cell 12.

In operation, the sample inlet and outlet ports 22, 24 are connected to suitable conduits for delivering fluid samples from a continually operating process or the like. It is contemplated that an absorption spectroscopy apparatus 10 constructed in accordance with the present disclosure has particular utility in monitoring the content of fluid, such as a gas or liquid, which is passing through a pipe or the like, and that the present apparatus 10 is useful in providing continuous analyses of the contents of gases passing through the pipe. In some cases it may be desirable to maintain the temperature and the pressure within the sample cell 12 at predetermined limits corresponding to the pressure and temperature conditions of the fluid prevailing in the pipe or process (and in some cases to minimize the adverse effects created by deposits formed on the light reflective surface of the side wall). Thus, as the fluid is brought into the sample cell 12 and returned to the original source of such fluid, the original process or other fluid source is in no way affected by the continual spectroscopy analysis. The present disclosure can be used in many applications including, but not limited to, as a gas analyzer, a replacement for a "White", "Wilks" or "Heriot-Watt" cell resonators, as part of a low-cost engine emissions analyzer, as part of a gas (e.g., carbon monoxide) detector for home or commercial use, as part of a gas leak detector, as part of a breath analyzer, and can be made to be used with liquids.

Figure 4:
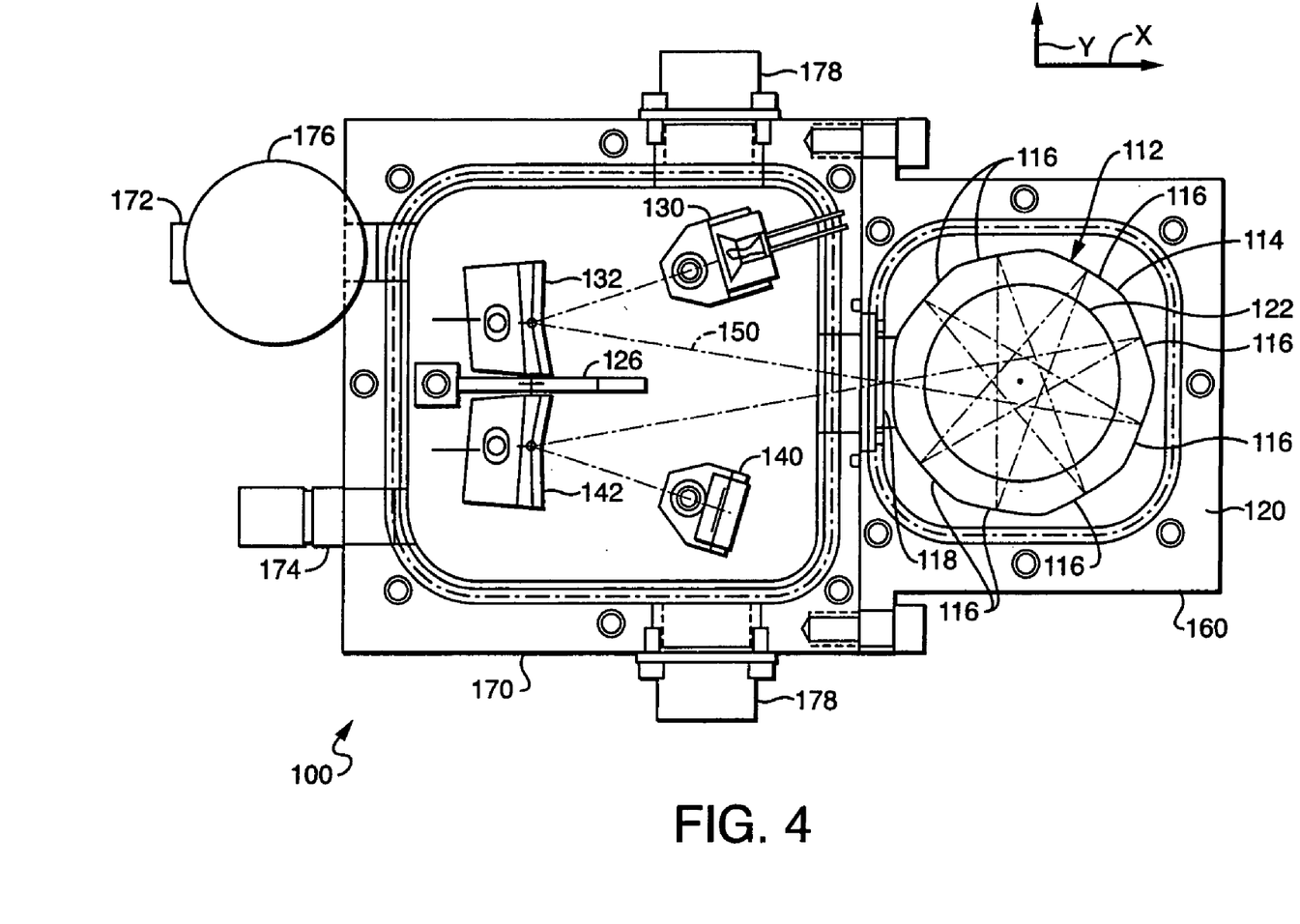
FIG. 4 is a top plan view of another exemplary embodiment of an improved absorption spectroscopy apparatus constructed in accordance with the present disclosure and including launch and collection reflectors and a multi-pass cell, wherein a trace of a light ray is shown reflecting off the launch and collection reflectors and completing multiple passes through the cell.
Figure 5:
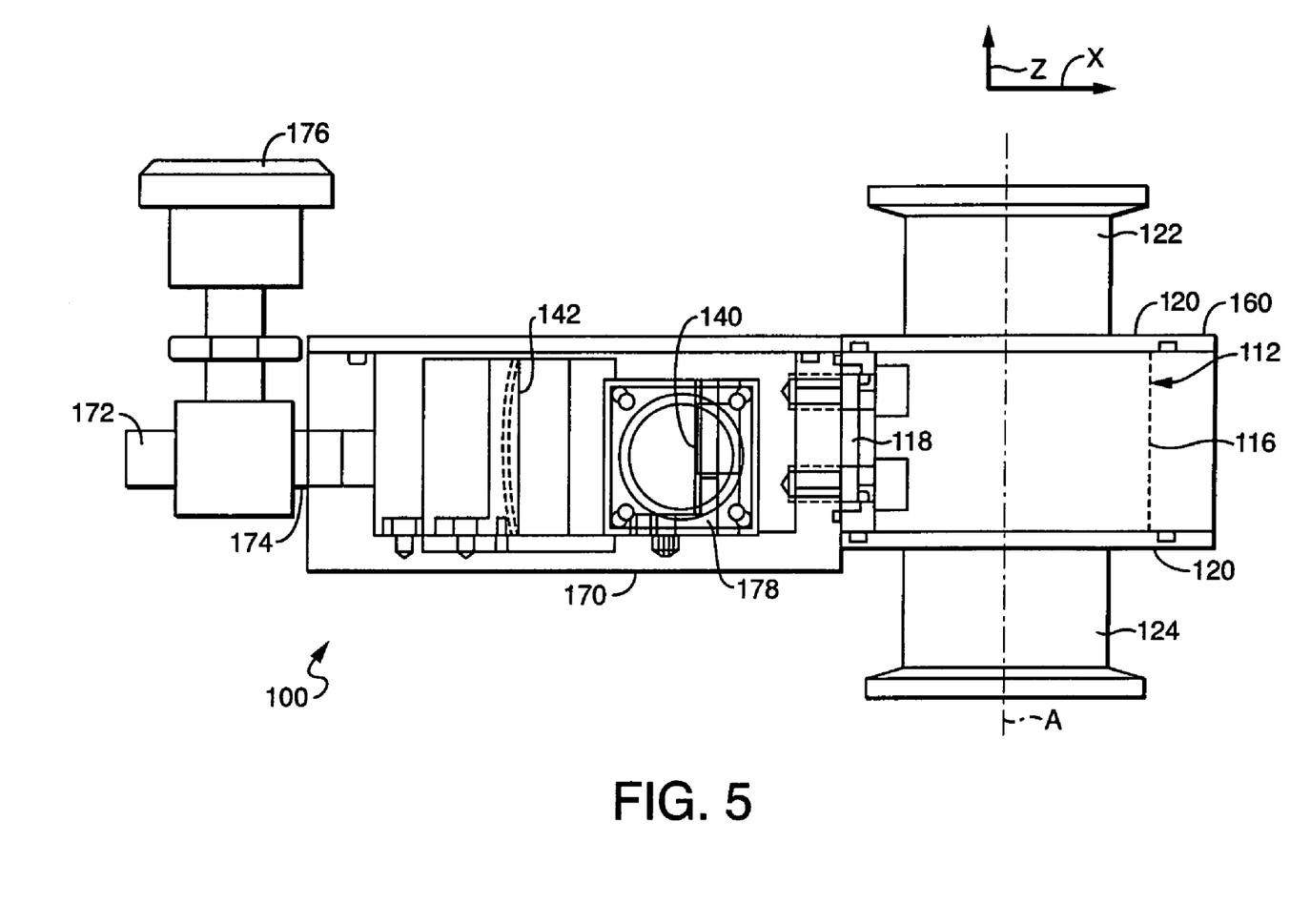
FIG. 5 is a side elevation view of the absorption spectroscopy apparatus of FIG. 4.

Referring now to FIGS. 4 and 5, another exemplary embodiment of an improved absorption spectroscopy apparatus 100 constructed in accordance with the present disclosure is shown. The apparatus 100 of FIGS. 4 and 5 is similar to the apparatus 10 of FIGS. 1 and 2 such that similar elements have the same reference numeral preceded by a "1". The apparatus 100 includes a light source 130 and a light detector 140, launch and collection reflectors 132, 142 and a multi-pass sample cell 112, and a trace of a light ray 150 is shown in FIG. 4 reflecting off the launch and collection reflectors 132, 142 and completing multiple passes through the cell 12. The apparatus 100 includes a cell housing 160 defining the multi-pass sample cell 112 and a source/collection housing 170, which holds the launch and the collection reflectors 132, 142 as well as the source 130 and the detector 140 packages. According to one exemplary embodiment, the source/collection housing 170 is filled with dry nitrogen or argon (no IR signature) and sealed-off from the gas stream passing the cell housing 160. The source/collection housing 170 can include inlet and outlet passages 172, 174 and a valve assembly 176 for filling the source/collection housing 170 with the dry nitrogen or argon, and access port assemblies 178 for the source 130 and detector 140 packages, as shown.

Figure 6:
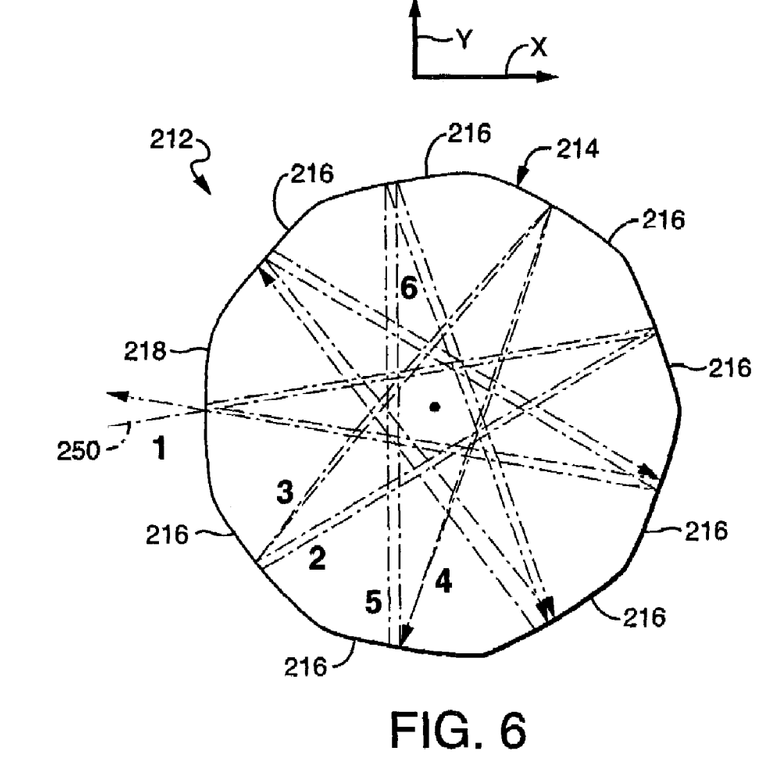
FIG. 6 is a schematic top view of an additional exemplary embodiment of an improved absorption spectroscopy apparatus including a multi-pass cell constructed in accordance with the present disclosure, wherein a trace of a light ray is shown completing multiple passes through the cell.
Figure 7:
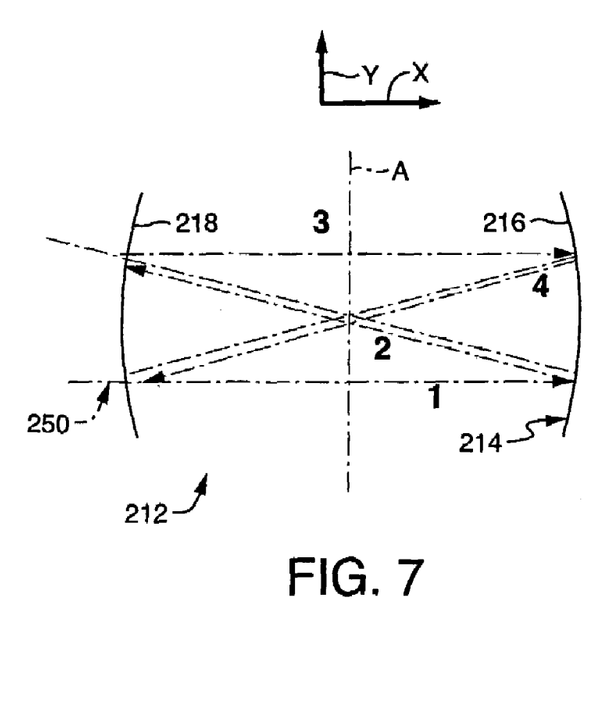
FIG. 7 is a schematic side view of the absorption spectroscopy apparatus of FIG. 6.

Referring now to FIGS. 6 and 7, a further exemplary embodiment of an improved multi-pass, fluid sample cell 212 constructed in accordance with the present disclosure is shown. The cell 212 of FIGS. 6 and 7 is similar to the multi-pass, fluid sample cell 12 of FIGS. 1 and 2 such that similar elements have the same reference numeral preceded by a "2". In the cell 212 of FIGS. 6 and 7, however, each of the reflective segments 216 of the side wall 214 of the cell 212 has a cross-section taken along a plane extending perpendicular to the axis (i.e., the x-y plane as illustrated in the drawings) that is planar with respect to the axis A. In addition, each of the reflective segments 216 of the side wall 214 of the cell 212 has a cross-section taken along a plane extending parallel to the axis A (e.g., the x-z plane as illustrated in the drawings) that is concave with respect to the axis A. A trace of a light ray 250 is shown in FIG. 4 completing multiple passes through the cell 212, and successive reflections of the light ray 250 are numbered 1, 2, 3, 4, 5 and 6. As shown, a light ray directed at an angle into the cell 212 (i.e., off plane) is reflected at least twice off each reflective segment 216 to thereby increase the overall path length of the light ray 250.

Figure 8:
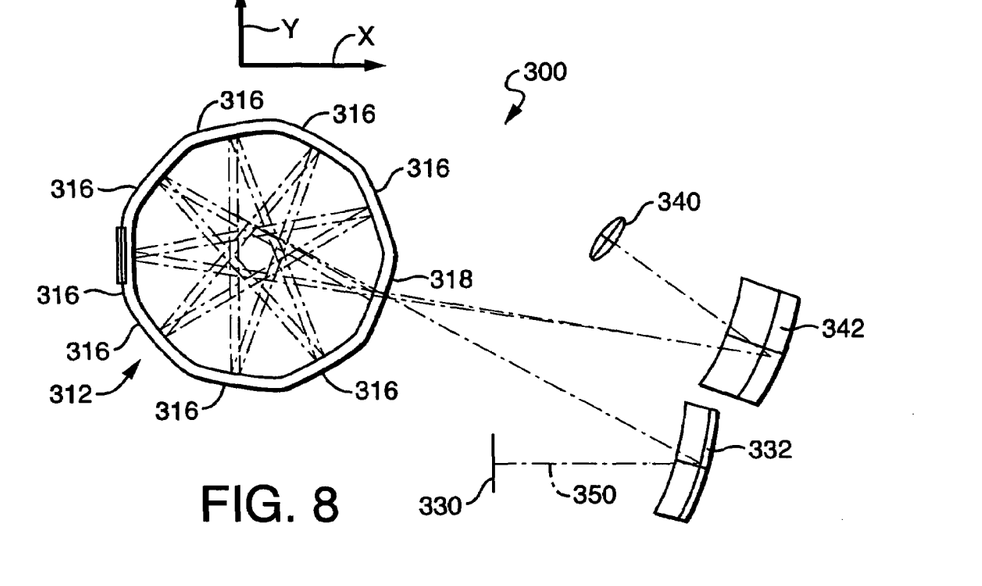
FIG. 8 is a schematic top view of a further exemplary embodiment of an improved absorption spectroscopy apparatus constructed in accordance with the present disclosure and including launch and collection reflectors and a multi-pass cell, wherein a trace of a light ray is shown reflecting off the launch and collection reflectors and completing multiple passes through the cell.
Figure 9:
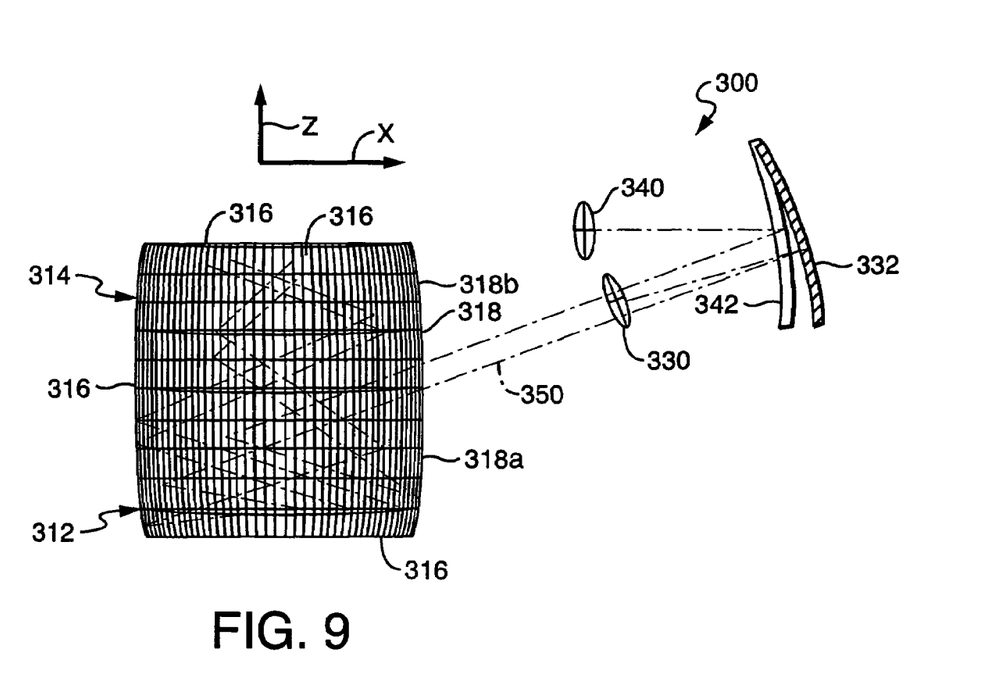
FIG. 9 is a schematic side view of the absorption spectroscopy apparatus of FIG. 8.

Referring now to FIGS. 8 and 9, a further exemplary embodiment of an improved absorption spectroscopy apparatus 300 constructed in accordance with the present disclosure is shown. The apparatus 300 of FIGS. 8 and 9 is similar to the apparatus 10 of FIGS. 1 and 2 such that similar elements have the same reference numeral preceded by a "3". In the apparatus 300 of FIGS. 8 and 9, however, each of the reflective segments 316 of the side wall 314 of the cell 312 has a cross-section taken along a plane extending parallel to the axis A of the cell 312 (e.g., the x-z plane as illustrated in the drawings) that is concave with respect to the axis A.

The segments 316 of the side wall 314 of the cell 312, therefore, include toroidal reflective surfaces facing the axis A of the sample cell. The toroidal reflective surfaces 316 act to focus light beams that are reflected off the surfaces, such that laser, incoherent, or non-collimated infrared light rays can be directed into the cell 312 and reflected through the cell, without a significant portion of the rays being lost out of the ends of the cell 312. The term toroidal surface as used herein is intended to mean a radially outer portion of a surface generated by a closed curve rotating about, but not intersecting or containing in its own plane the axis A of the cell, or in other words a radially outer segment of a surface of a donut.

The light transmissive segment 318 of the side wall 314 includes a light transparent portion 318b for admitting a ray of light directed into the cell 312 and for allowing a ray of light to be directed out of the cell 312. The light transparent portion 318b is located nearer to one end of the segment 318. The light transmissive segment 318 of the side wall 314 also includes a reflective portion 318a, such that that portion 318a of the segment 318 can be used to further reflect, and increase, the path length of the light ray 350.

Path length is further enhanced in the cell 312 of FIGS. 8 and 9, without increasing the package size, but by merely adjusting the launch optic angle, the source angle, or both. By properly adjusting the light's "out of plane" launch angle, light entering the cavity 312 may then be reflected off each cavity wall segment 316 multiple times, before exiting, so that the path length is significantly increased, as shown in FIGS. 8 and 9. The entry angle and z-curvature determine the number of times light is reflected around the cell 312, and thus the multiple of the "in plane" single pass path length.

Figure 10:
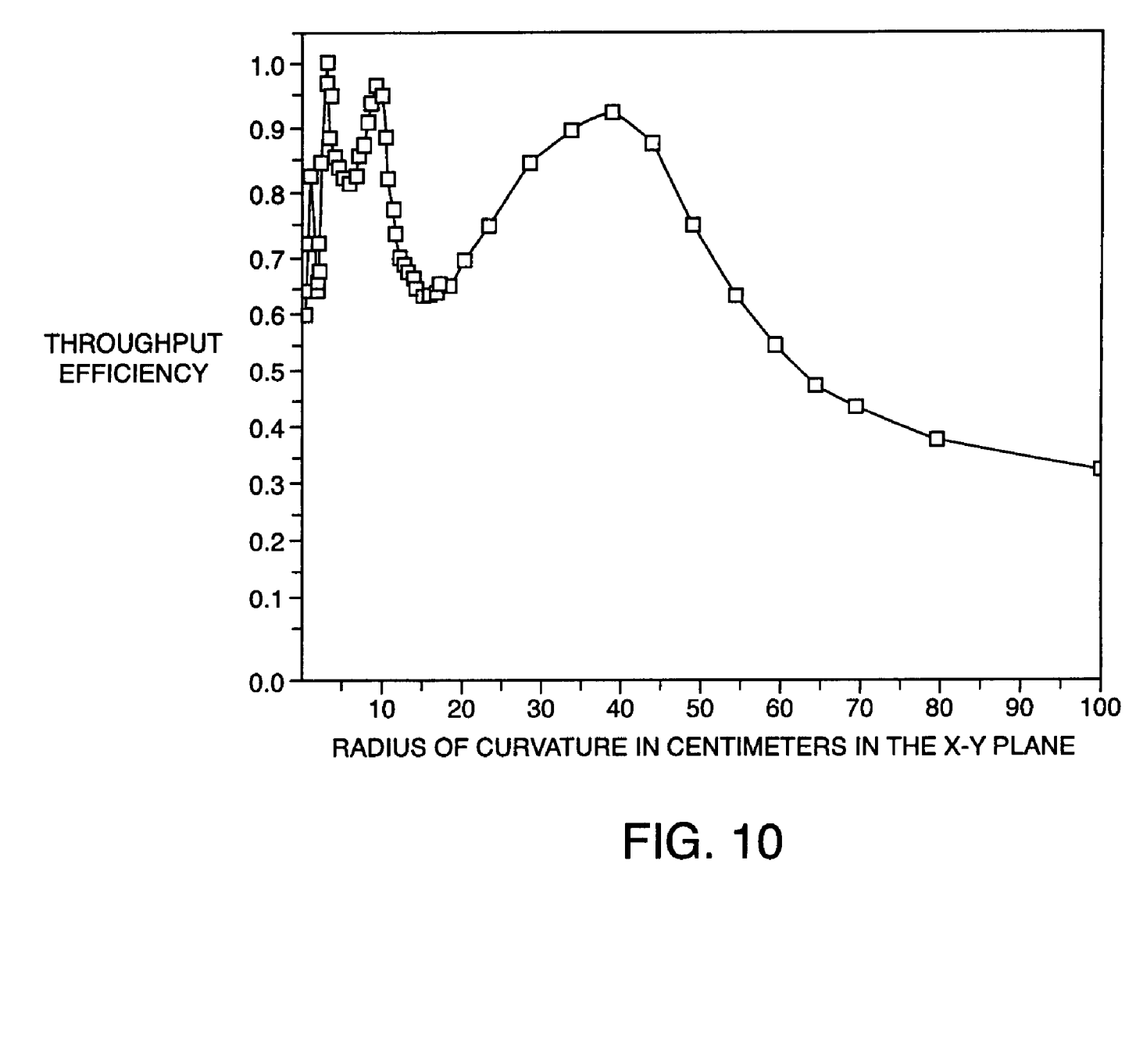
FIGS. 10 and 11 are graphs of optical efficiency of the multi-pass cell of FIGS. 8 and 9 as a function of a surface radius of curvature of segments of the cell in the x-y plane.
Figure 11:
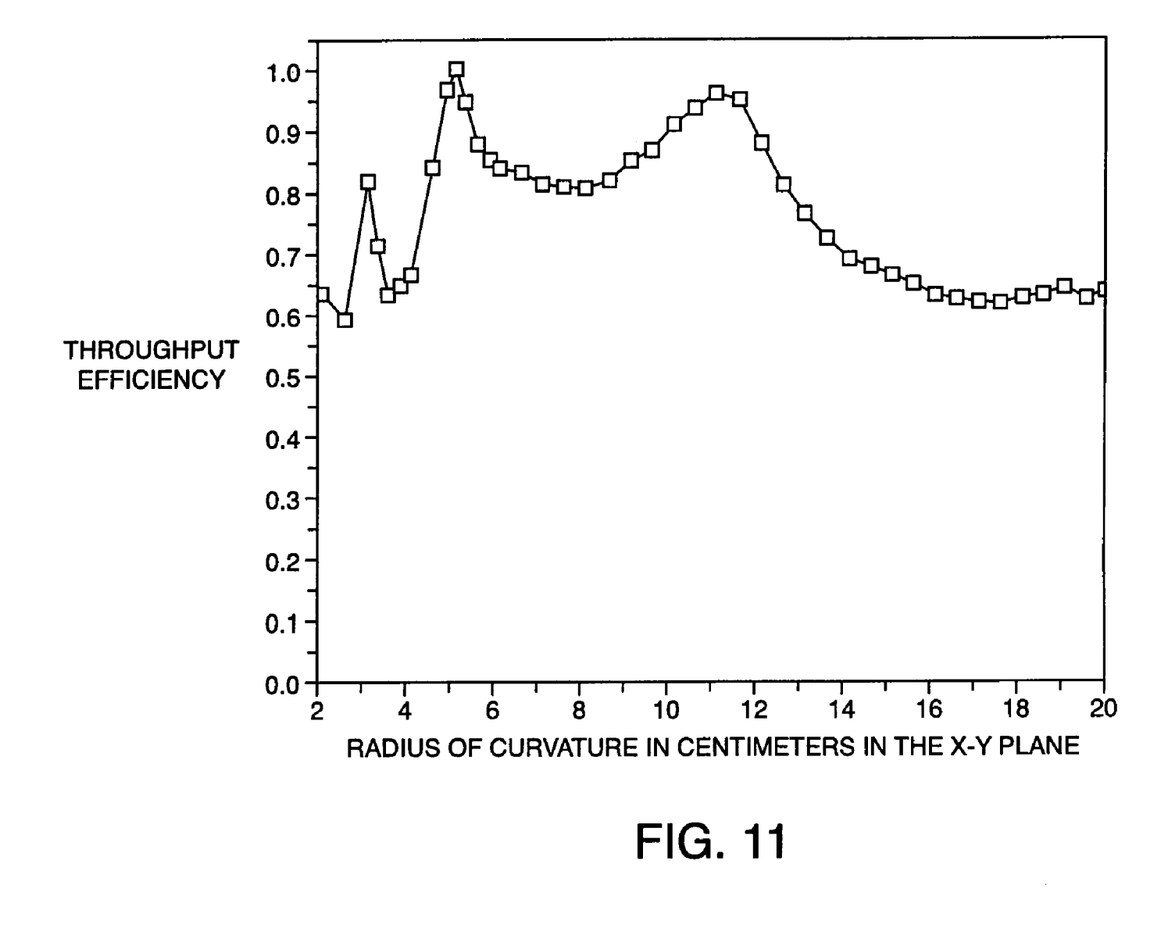
Figure 12A:
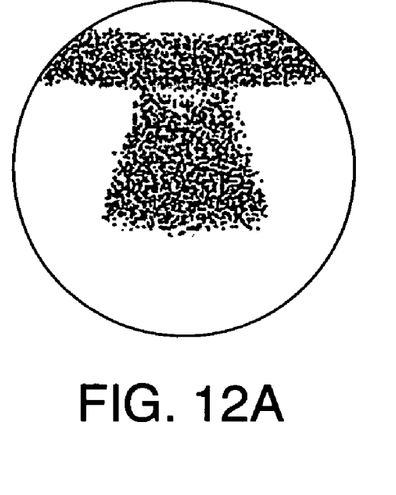
FIGS. 12a–12d are transmitted light power distribution graphs for the multi-pass cell of FIGS. 8 and 9 as a function of a surface radius of curvature of segments of the cell in the x-y plane.
Figure 12B:
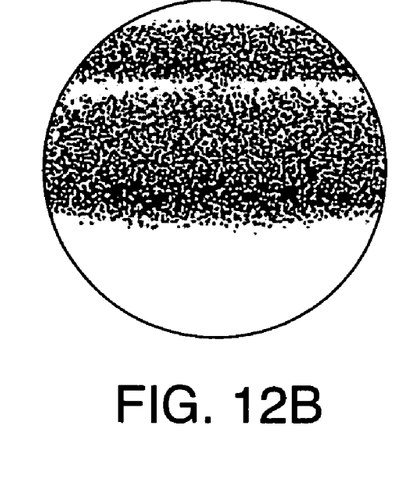
Figure 12C:
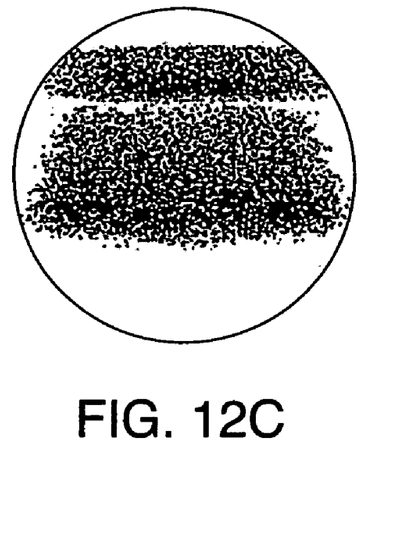
Figure 12D:
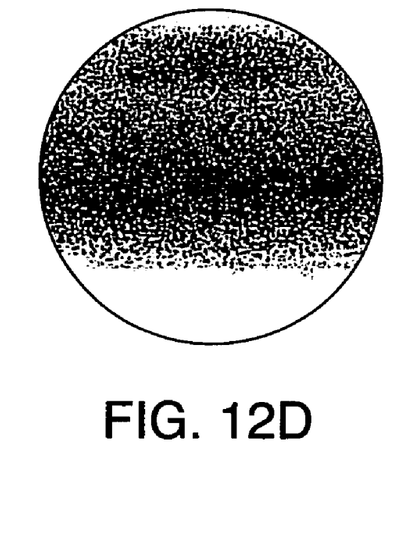

The radii of curvature of the reflective surfaces 316 in both the x-y plane and the x-z plane define the toroidal shape of the segments 316 of the side wall 314, and can be selected for optimum throughput efficiency as well as maximum design tolerance. This is illustrated by using 3-D Monte Carlo optical ray trace simulations, and plotting throughput efficiency as a function of radius of curvature of the segments 316 in the x-y plane, as shown in FIGS. 10 and 11. FIG. 11 is an enlargement of a lower portion of FIG. 10. FIGS. 10 and 11 show that, with a radius of curvature of 5 cm of the segments 316 in the x-y plane yield an optimum throughput efficiency of 1.0. Compared to the apparatus 10 of FIGS. 1 and 2, optical efficiency may be improved by a factor of three.

The added cavity wall curvature focuses divergent light sources in all dimensions, and effectively collimates the beam to yield a more uniform light power distribution pattern on the surface of the detector 340. By choosing a design with a longitudinal radius of curvature corresponding to an optical throughput efficiency in the plateau region of FIGS. 10 and 11, small deviations from the nominal radius, due to, for example, manufacturing errors, have minimum impact on the optical performance. The toroidal cavity 312 enables higher throughput efficiency, for longer path lengths, and more uniform distribution of power on the detector package. Transmitted light power distribution on a detector package using toroidal cavity optics with longitudinal radii of curvatures corresponding to $r=\infty$ (shown as 0 cm in charts of FIGS. 10 and 11), $r=4$ cm, $r=6$ cm, and $r=40$ cm are shown respectively in FIGS. 12a–12d. The present disclosure, therefore, enables control of throughput efficiency, path length, and spatial uniformity of incident power through proper selection of cavity surface radii, cavity diameter, and number of reflective facets.

Figure 13:
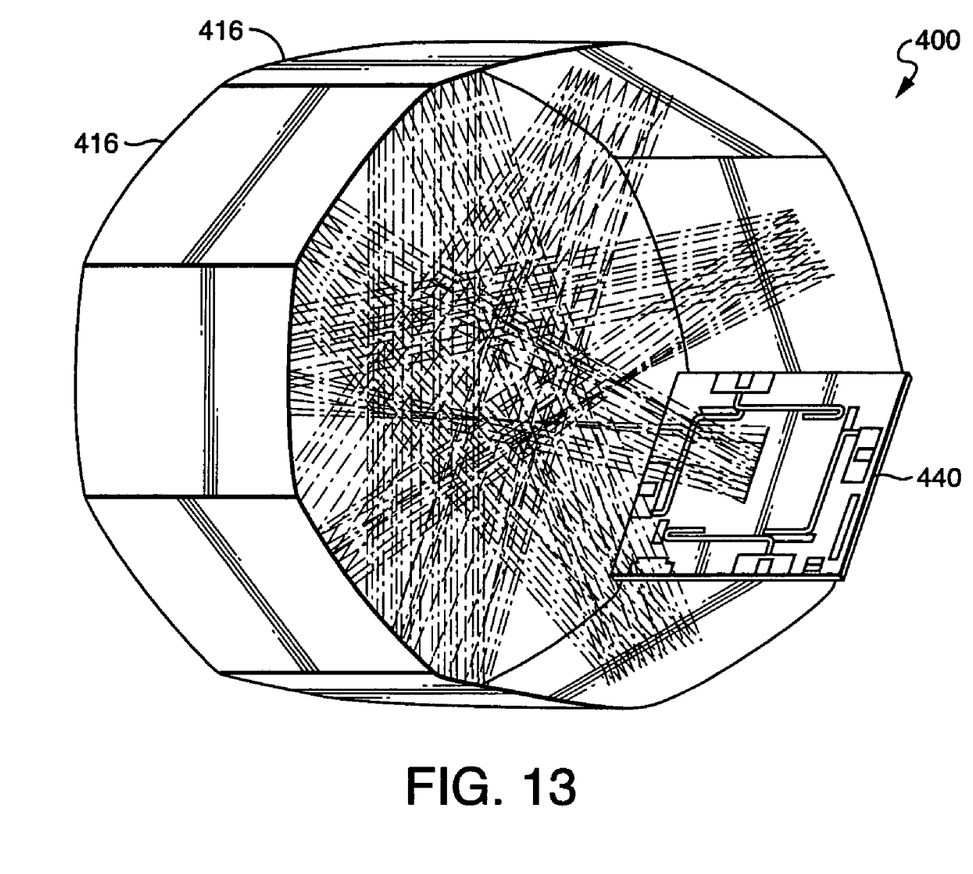
FIG. 13 is a schematic perspective view of an another exemplary embodiment of an improved absorption spectroscopy apparatus constructed in accordance with the present disclosure and including launch and collection reflectors and a multi-pass cell, wherein a trace of a light ray is shown reflecting off the launch and collection reflectors and completing multiple passes through the cell.

According to another exemplary embodiment 400, as shown in FIG. 13, the entire source, detector, launch and collect optics housed in a separate component housing, are replaced with a single emitter/detector infrared transceiver 440, tuned to the appropriate wavelength for selective gas/chemical analysis. For example, a wavelength-tuned, integrated infrared source/detector device (i.e. hot bolometer) described in U.S. Pat. No. 6,373,056, can be positioned within the cell. The device interfaces with the cavity optic, and is aligned such that emitted light is reflected around the cavity 412, and back to the device 440. The device rapidly reaches thermal equilibrium with its emitted and absorbed radiation. When a gas having an absorption line matching or falling within the band of the tuned device is introduced in the cavity 412, power is absorbed by the gas, and the device 440 equilibrates at a new temperature. Gas concentration is determined from the measured change in temperature, or measured change in some other parameter (resistance, drive power, voltage, or current) coupled to the temperature change.

The present disclosure, therefore, provides an improved "multi-pass" sample cell that causes light to pass through a very large percentage of a sample contained in the cell. The improved sample cell prevents the loss of significant amounts of light through ends of the cell and increases the throughput of the cell. In addition, the improved cell is compact, robust, and relatively easy to manufacture.

Certain modifications and improvements to the exemplary embodiments of the present disclosure will occur to those skilled in the art upon a reading of the foregoing description. It should be understood that all such modifications and improvements have been deleted herein for the sake of conciseness and readability but are properly within the scope of the present disclosure as recited in the following claims.

What is claimed is:

1. An absorption spectroscopy apparatus comprising a sample cell including a central axis and a side wall coaxially positioned about the central axis and defining a generally circular cross-section of the sample cell as taken along a plane extending perpendicular to the axis of the cell, wherein the generally circular cross-section of the sample cell has an average radius, and wherein the side wall includes a plurality of light reflective segments arrayed about the axis, wherein each reflective segment has a cross-section taken along a plane extending perpendicular to the axis of the cell that is concave with respect to the axis, and the concave cross-section of each segment has an average radius that is unequal to the average radius of the generally circular cross-section of the sample cell.

2. An absorption spectroscopy apparatus according to claim 1, wherein the average radii of the concave cross-sections of the segments of the side wall are equal.

3. An absorption spectroscopy apparatus according to claim 2, wherein the average radii of the concave cross-sections of the segments of the side wall are each greater than the average radius of the generally circular cross-section of the sample cell.

4. An absorption spectroscopy apparatus according to claim 3, wherein the average radii of the concave cross-sections of the segments of the side wall are each at least two times greater than the average radius of the generally circular cross-section of the sample cell.

5. An absorption spectroscopy apparatus according to claim 1, wherein the average radii of the concave cross-sections of the segments of the side wall each comprises a constant radius.

6. An absorption spectroscopy apparatus according to claim 1, wherein each of the average radii of the concave cross-sections of the reflective segments of the side wall pass through the axis of the sample cell.

7. An absorption spectroscopy apparatus according to claim 1, wherein the light reflective segments of the side wall are equally arrayed about the axis.

8. An absorption spectroscopy apparatus according to claim 1, wherein each of the reflective segments of the side wall of the cell has a cross-section taken along a plane extending parallel to the axis of the cell that is planar.

9. An absorption spectroscopy apparatus according to claim 1, wherein each of the reflective segments of the side wall of the cell has a cross-section taken along a plane extending parallel to the axis of the cell that is concave with respect to the axis.

10. An absorption spectroscopy apparatus according to claim 9, wherein at least one of the segments of the side wall includes a light transparent portion for admitting a ray of light directed into the cell and for allowing a ray of light to be directed out of the cell, and wherein the light transparent portion is located nearer to one end of the segment.

11. An absorption spectroscopy apparatus according to claim 1, further comprising an optical gas sensor located within the cell and including an emitter for generating a ray of light and directing the ray of light to one of the reflective segments of the side wall of the cell, and a detector for receiving the ray of light from one of the reflective segments of the side wall of the cell.

12. An absorption spectroscopy apparatus according to claim 1, wherein the side wall further includes at least one light-transparent segment and the apparatus further comprises at least one launch/collection reflector adapted to direct light through the light-transparent segment and into the cell and receive light directed out of the light-transparent segment from the cell.

13. An absorption spectroscopy apparatus according to claim 12, wherein the launch/collection reflector comprises separate source and collection reflectors.

14. An absorption spectroscopy apparatus according to claim 12, wherein the launch/collection reflector has a concave cross-section as viewed from an end of the launch/collection reflector.

15. An absorption spectroscopy apparatus according to claim 12, wherein the launch/collection reflector has a concave cross-section as viewed from a side of the launch/collection reflector.

16. An absorption spectroscopy apparatus according to claim 12, further comprising an emitter for generating a ray of light and directing the ray of light to the launch/collection reflector, and a detector for receiving the ray of light from the launch/collection reflector.

17. An absorption spectroscopy apparatus according to claim 12, further comprising an emitter for generating a ray of light and directing the ray of light to the launch/collection reflector, and a detector for receiving the ray of light from the launch/collection reflector, and wherein the emitter comprises a wide angle, low frequency thermal emitter and the detector comprises a wide angle, low frequency thermal detector.

18. An absorption spectroscopy apparatus according to claim 1, further comprising end walls closing ends of the side wall of the cell.

19. An absorption spectroscopy apparatus according to claim 18, wherein the end walls have reflective surfaces facing inwardly with respect to the cell.

20. An absorption spectroscopy apparatus according to claim 18, wherein the end walls include a fluid inlet and a fluid outlet.

21. An absorption spectroscopy apparatus according to claim 1, wherein:
   each of the reflective segments of the side wall of the cell has a cross-section taken along a plane extending parallel to the axis of the cell that is concave with respect to the axis;
   at least one of the reflective segments of the side wall includes a light transparent portion for admitting a ray of light directed into the cell and for allowing a ray of light to be directed out of the cell, and wherein the light transparent portion is located nearer to one end of the segment;
   the apparatus further comprises at least one launch/collection reflector adapted to direct light through the light transparent portion of the cell and receive light directed out of the light transparent portion of the cell; and
   wherein the launch/collection reflector are positioned to direct a beam of light through the light transparent portion such that the beam is oriented at an angle other than perpendicular with respect to the axis of the cell.

* * * * *